United States Patent [19]

Heyden

[11] Patent Number: 4,865,595
[45] Date of Patent: Sep. 12, 1989

[54] DRAINAGE DEVICE FOR URINE

[76] Inventor: Eugene L. Heyden, S. 627 Bernard, #8, Spokane, Wash. 99204

[21] Appl. No.: 166,200

[22] Filed: Mar. 10, 1988

Related U.S. Application Data

[63] Continuation-in-part of Ser. No. 48,993, Apr. 23, 1987, Pat. No. 4,731,064, which is a continuation of Ser. No. 834,560, Feb. 28, 1986, abandoned.

[51] Int. Cl.⁴ ............................................... A61F 5/44
[52] U.S. Cl. .................... 604/352; 156/289; 128/844
[58] Field of Search ............... 156/244, 289; 128/842, 128/844; 604/349–355

[56] References Cited

U.S. PATENT DOCUMENTS

| | | | |
|---|---|---|---|
| 2,604,092 | 7/1952 | Brown et al. | 128/132 |
| 3,018,484 | 7/1958 | Koehn | 2/21 |
| 3,138,160 | 6/1964 | Stoutenburgh | 604/351 |
| 3,364,932 | 4/1965 | Beach | 128/295 |
| 3,403,682 | 12/1965 | McDonell | 128/295 |
| 3,648,700 | 3/1971 | Warner | 128/294 |
| 4,378,018 | 6/1981 | Alexander | 128/295 |
| 4,534,768 | 8/1985 | Osburn et al. | 604/355 |
| 4,626,250 | 12/1986 | Schneider | 604/353 |
| 4,731,064 | 3/1988 | Heyden | 604/352 |

FOREIGN PATENT DOCUMENTS 2016929  9/1979  United Kingdom .

Primary Examiner—Jerome L. Kruther, Jr.

[57] ABSTRACT

A drainage device for urine, the device being of the external or condom catheter variety and incorporating at least one adhesive-surfaced foamed tape bonded to the inner surface of a flexible catheter sleeve member formed into a catheter roll. The foamed tape, or a plurality of foamed tapes, extend away from the catheter roll and are provided to adhesively attach to the penis to prevent a displacement of the penis from an intended position within the device as the catheter roll is unrolled over the penis.

4 Claims, 2 Drawing Sheets

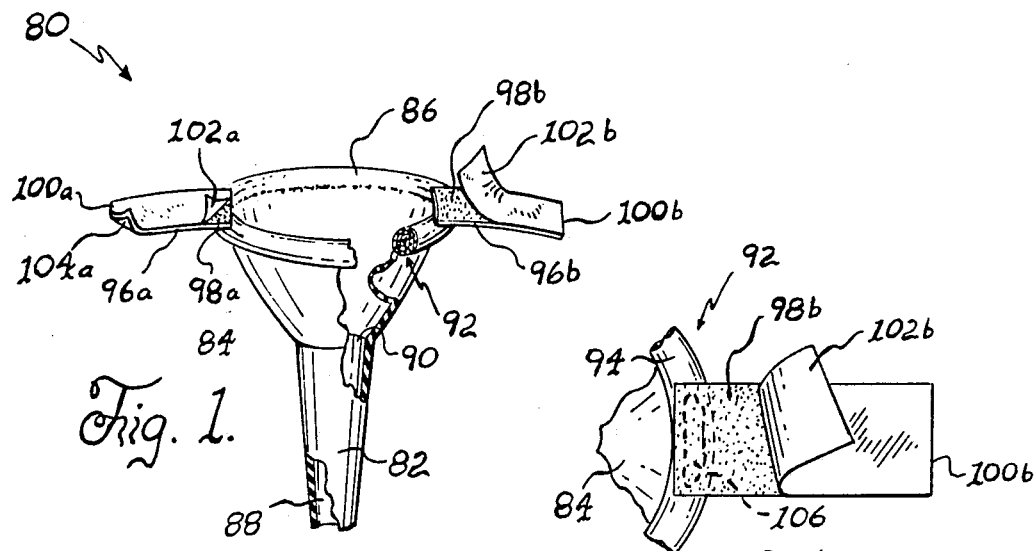
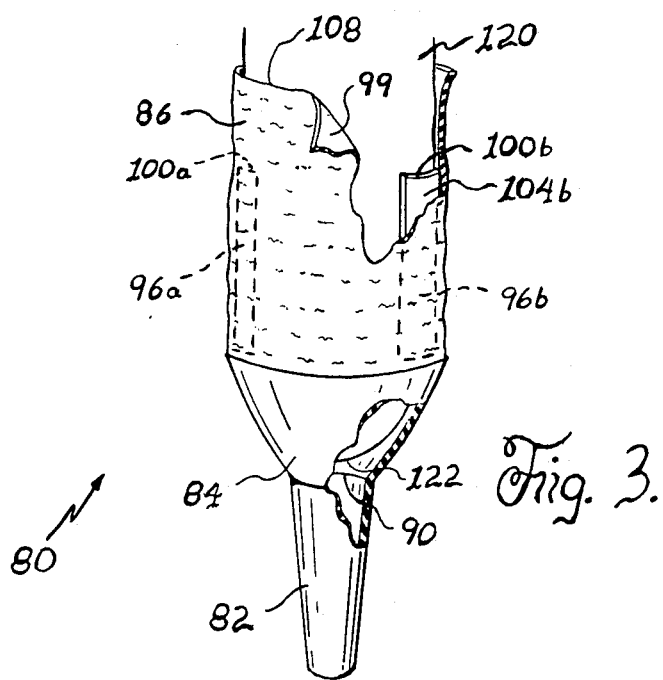

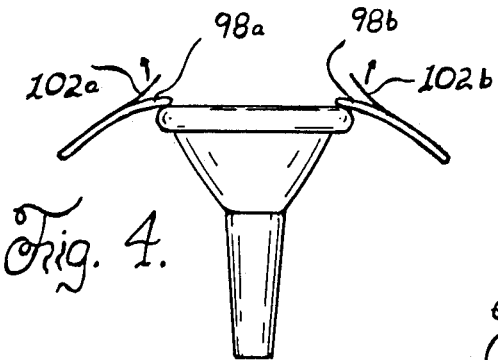
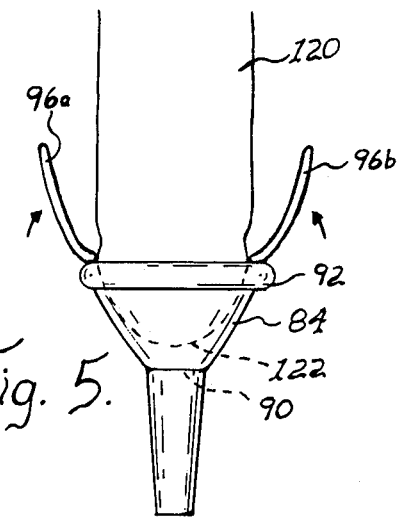
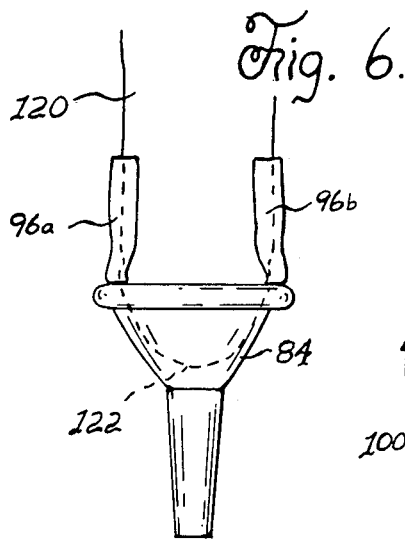
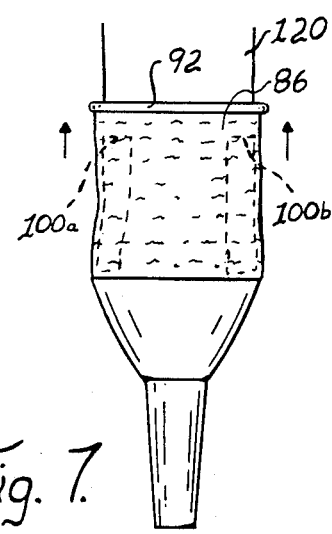
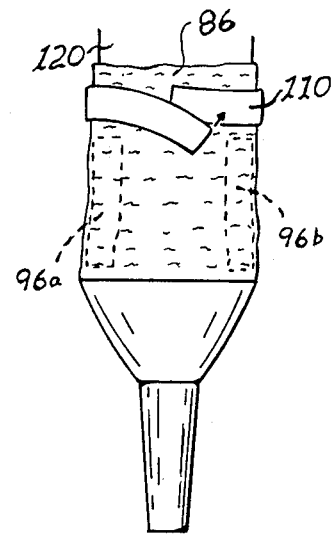

DRAINAGE DEVICE FOR URINE

CROSS-REFERENCE TO RELATED APPLICATION

This application is a continuation-in-part of the application entitled URINE DRAINAGE DEVICE, Ser. No. 048,993, filed Apr. 23, 1987 now U.S. Pat. No. 4,731,064 by the same inventor and issued on Mar. 15, 1988 which is a continuation of 06/834,560 filed 2/28/86 now abandoned.

BACKGROUND OF THE INVENTION

This invention relates to external catheters in use with male patients, and more particularly to the improvement wherein one or a plurality of flap member components are provided therewith for assisting in the application of the catheter upon the penis.

It is commonplace in a variety of clinical situations for patients to lose control of the discharge of urine. It is generally preferable to avoid transurethral catheterization of the urinary bladder, as infection, discomfort, or internal injury can result. Accordingly, an external, condom-like catheter is often employed as an alternative to an invasive catheterization of the male patient.

The typical external catheter, also called a "condom" or "Texas" catheter, generally comprises an elongated, circularly tubular device of one-piece construction having a stem section defining a fluid passage, an intermediately-positioned conical or cup-shaped mid-portion providing a forward discharge opening in communication with the fluid passage, and a relatively flexible, thin-walled sleeve member dimensioned to extend over and cover the penis. In catheters of this type, the sleeve member is prepared in an initial rolled-up attitude to reside in the vicinity of the conical mid-portion, and is manually unrolled over the penis during the application procedure. Also in catheters of this type, the sheath member may have an adhesive substance on it inner wall surface to adhesively engage the penis and to effect a liquid-tight seal. Alternatively, the catheter may be constructed without such an inner-surface adhesive on its sleeve member, whereupon an encircling band of adhesive-surfaced foam tape, placed about the unrolled portion of the device, is intended to effect a liquid-tight seal between catheter and penis and to help hold the device in place, according to one method of practice. Additionally in catheters of this type, the stem section of the device may present a dilation at the base of the mid-portion which serves as a surge chamber and acts as an anti-kink mechanism.

To function as intended, it is desirable to place and maintain the free end of the penis in near approximation to the forward discharge opening of the external catheter. When the free end of the penis is maintained within the catheter in such a position during external catheterization, a twisting, collapsing, or kinking of the catheter to a degree which restricts the outflow of urine or contributes to an ill-fitting of the device is largely prevented.

Unfortunately, improper positioning and poor fit are common problems associated with the typical external or condom-like catheter. Often encountered when applying the device to the penis are problems which occur when the catheter sleeve member is unrolled over the penis. It has been observed that the act of unrolling the sleeve member of the catheter tends to push the free end of the penis away from the forward discharge opening and out of an intended position within the conical mid-portion of the catheter, contributing to an improper fit of the device upon the penis. It has also been observed that the relative looseness of the penile skin tends to cause the same to be pushed ahead of the catheter roll as the sleeve member of the catheter is unrolled, displacing the penile skin rearwardly away from a normal, relaxed position. In this eventually, after the catheter is unrolled, the penile skin will then return to a relaxed state and cause the free end of the penis to displace and withdraw from the intended position within the mid-portion of the catheter, leading to the aforementioned problems associated with an improper positioning and fit of the device.

In the related, above-identified U.S. patent application, herein incorporated by reference, a substantial improvement in the external, condom-like catheter is disclosed and entails the provision of one or more flap members which are intergral with the device and which project from an interior location on or near the conical mid-portion of the catheter. The flap member or members provide an adhesive surface which can adhesively engage the penis prior to an unrolling of a rearward portion (or, as it is called in this disclosure, a sleeve member) of the catheter over the penis, in address of the above-mentioned problems associated with the typical external or condom-like catheter. Removable cover slips may be provided to protect the adhesive surface of the flap member (s) prior to an intended procedure for applying the catheter to the penis. According to the prior disclosure, the flap member or members may be a formed and component extention of the elastomer material common to the remainder of the catheter device. Alternatively, the flap member or members of the parent disclosure may be constructed separately and then suitably bonded to the catheter at an appropriate location.

With the foregoing in mind, it has been found suitable to use, as flap members, short strips of medically-approved, adhesive-surfaced flexible foamed tapes, bonded on their non-adhesive side to suitable catheter locations. In a further advance of the art, it has been discovered that the foamed tapes can be attached to what may be considered an external location on the catheter, rather than attached to what may ordinarily be regarded as in inner location on the catheter and a more difficult attachment to achieve.

It is, therefore, one object of the present invention to provide a condom catheter with members which will act to prevent an unrolling sleeve member from pushing the free end of the penis away from a forward discharge opening and which will prevent the same from pushing the penile skin ahead of the roll during the application procedure.

It is a further object of the present invention to provide a method of manufacturing an external catheter having one or a plurality of secondarily-attached flap members connected to said catheter in a comparatively simplified manner.

These and other objects will become readily apparent as the written disclosure, in its entirety, is studied in connection with the attending drawing.

SUMMARY OF THE INVENTION

With the above considerations in mind, the present invention provides an external and condom-like catheter, hereinafter primarily referred to as an external catheter, formed principally of a latex or a similar material and generally tubular in its longitudinal progression. The device includes a stem section defining a fluid passage, and intermediate, conical or cup-shaped mid-portion presenting a fluid discharge opening in fluid communication with said fluid passage, and a sleeve member having a relatively thin, relatively flexible wall dimensioned to circumferentially and substantially cover the penis. The sleeve member is prepared in an initial roller-up attitude or state at the time of manufacture, effecting a catheter roll in the vicinity of said conical portion wherein the internal surface of said sleeve member is externally exposed. According to the present invention in the preferred embodiment, and as would be accomplished by a secondary operation, two strips of adhesive-surfaced foamed tape are adhesively bonded to the catheter roll at opposing, uppermost locations, with the adhesive surface of each tape facing away from the catheter roll and the non-adhesive side attached to the catheter roll. So placed and bonded, the tapes are, in effect, externally connected to what, in actuality, are internal surface locations on the catheter's sleeve member, in that the catheter roll externally exposes portions of the inner surface of said sleeve member. Additionally, removable cover slips are associated with the adhesive surface of the tapes, to be removed and discarded prior to the intended application procedure for applying the device upon the penis. The procedure advanced by this disclosure entails a removal of the cover slips, a placement of the free end of the penis within the mid-portion of the catheter, an adhesive attachment of the foamed tape flap members to opposing sides of the penis, followed by an act of unrolling and an extending of the sleeve member of the catheter over the penis and beyond the foamed tapes, whereupon the tapes prevent a displacement of the free end of the penis as the catheter is unrolled.

BRIEF DESCRIPTION OF THE DRAWING

The invention can best be understood in conjunction with the accompanying drawing in which:

FIG. 1 is a perspective view of the catheter in the preferred embodiment, having portions thereof cut away or otherwise adapted for illustrative purposes;

FIG. 2 is an enlarged, partial top view of the device of FIG. 1;

FIG. 3 is a perspective view of the device of FIGS. 1 and 2 following an application of the catheter to the penis as intended according to this disclosure, the view modified for illustrative purposes; and FIGS. 4 through 8 illustrate the intended procedure for applying the device satisfactorily upon the penis.

DETAILED DESCRIPTION OF THE PREFERRED EMBODIMENT

With particular reference to FIGS. 1 through 2 of the drawing, the invention in the preferred embodiment comprises a flexible-walled external catheter 80 of generally tubular construction including a stem section 82 defining a fluid passage 88, a conical mid-portion 84 emerging and enlarging from said stem section, and an opposing, comparatively thin-walled and more flexible sleeve member 86 of substantially uniform circumference emerging from the catheter's mid-portion and shown in FIGS. 1 and 2 in a rolled-up state. The sleeve member 86 is particularly dimensioned in both circumferential and longitudinal extent so as to fulfill its intended purpose of accommodating and substantially covering the penis when unrolled thereupon. The catheter 80 is largely constructed of a flexible material such as a latex or a similar elastomer, with each of the above-named catheter portions constructed about a longitudinal axis and in axial allignment with each other. A fluid discharge opening 90, common to both the stem section 82 and the mid-portion 84 of the catheter, is defined within the catheter and allows fluid communication to exist between the catheter's mid-portion and fluid passage 88. During its use as a device for the drainage of urine, the stem section thereof is connected to a drainage tube for the transfer of urine to a drainage receptacle (not shown).

The catheter is shown in FIGS. 1 and 2 in a rolled-up state, according to the customary practice of outwardly rolling down the sleeve member 86 at the time of manufacture for removal from a mandrell and for a preparation of the catheter for application purposes, and is accordingly rolled down to an extent whereby the sleeve member is rolled up into a catheter roll 92 near the mid-portion 84 of the device. During the application and use of the device on the penis 120, it is intended that the sleeve member 86 be unrolled and extended thereover for urine drainage, as shown in FIG. 3, and remain satisfactorily extended thereover while the free end 122 of the penis resides substantially within the catheter mid-portion and in the vicinity of the fluid discharge opening 90.

Principle to the present invention is the outward exposure of the inner surface of the catheter's sleeve member 86, effected during roll formation. This inner surface is particularly identified by reference numeral 94 in both FIGS. 2 and 3. Also principle to the present invention is an attachment of a flap member or members, further identified herein as an adhesive-surfaced foamed tape or tapes, to appropriate locations on the outwardly-exposed, inner surface of said sleeve member, as evidenced in FIG. 2. The use of cut lengths of flexible, closed-cell foamed tape ¾" in width, having an adhesive surface carrying a removable cover slip and having an opposing, a non-adhesive side, has been found satisfactory in the practice of the present invention. The attachment between flap member and sleeve is intended to be performed by a secondary operation after the construction of the basic catheter as previously identified. As can be readily appreciated from a comparison between FIG. 3 and the two previous figures of the drawing, portions of said inner surface 94 which reside in the vicinity of the mid-portion 84 of the catheter are outwardly exposed when the sleeve member is in a complete or nearly complete rolled-up state. According to the purposes of the present invention, then, suitable internal catheter locations are thus outwardly exposed so as to readily allow an outwardly-achieved attachment of two opposing and outwardly extending adhesive-surfaced foamed tapes 96a and 96b to what are, in effect and actuality, opposing inner locations of the catheter. The foamed tapes, as shown in FIGS. 1 and 2, present with two protective, removable cover slips found commonly associated with adhesive-surfaced foamed tapes, with cover slip 102a associated with foamed tape 96a and cover slip 102b associated with foamed tape 96b, both before and after attachment of the foamed tapes to the catheter roll. The cover slips oppose the respective non-adhesive sides 104a and 104b of the foamed tapes, and serve to protect the respective adhesive surfaces of the foamed tapes until removed.

It is contemplated in the practice of the present invention that the foamed tapes be individually and securely bonded to the inner surface of the catheter sleeve member 86 at a location near the catheter mid-portion 84, such as would be accomplished by an attachment to the catheter roll 92. Attached or connected to the catheter roll at such a suitable general location, the use of the foamed tapes 96a and 96b, adhesively bonded at end portions to specific locations on the catheter roll and equally on the inner surface 94 of the sleeve member with their adhesive surfaces 98a and 98b facing away from the remainder of the catheter, readily lend themselves to the practice of the present invention.

With attention directed particularly to FIG. 2, the above-mentioned adhesive bonding between the foamed tapes and the catheter roll, which is to be regarded and understood as occurring between the non-adhesive sides 104a and 104b of the foamed tapes and the inner surface 94 of the sleeve member which has been outwardly exposed by catheter roll formation, is particularly evident. Further contemplated is the occurrence of the adhesive bond at a portion of each tape member which substantially opposes the free end of the foamed tape. The connection between foamed tape and sleeve member may be achieved by a suitable bonding agent, represented by reference numeral 106 and indirectly evident in the drawing by hidden line delineation. The bonding agent 106 may be a fast-drying contact cement applied to both the foamed tape and the catheter roll prior to a subsequent joining thereof to effect a bond between catheter and tape, or it may be of any other suitable bonding agent and method of bonding. It should be pointed out that the strength of the bond should be such that it would represent a substantially permanent bond, or at least be a bond which would require a determined effort to break, in excess of the forces normally exerted on the bond during the use of the adhesive tapes as intended.

In further view of FIG. 3, it is seen that the foamed tapes 96a and 96b are shorter in length than the extended length of the catheter sleeve member 86. It is intended according to the practice of the invention in the preferred embodiment that the sleeve member extend beyond the free ends 100a and 100b of the foamed tapes when the sleeve member is unrolled over the penis 120. A tape length on the order of 1 inch to 1 and ½ inches is considered to be an adequate length in most circumstances. (The foamed tapes may be cut to a shorter length then their provided length if it is advantagous to do so, as in the case of a penis of relatively short longitudinal extent.) By such an arrangement, the flow of urine along the sides of the foamed tapes is prevented from leaking out beyond the sleeve member by the extention of the sleeve member a suitable distance beyond the foamed tapes, particularly when the practice of the invention includes an encircling closure band 110, as shown in FIG. 8, and the closure band is favorably placed about the catheter's sleeve member between the free ends 100a and 100b of the foamed tapes at what may be regarded as the free end 108 of the sleeve member. The closure band 110, which may comprise a five to six-inch length of flexible, adhesive-surfaced tape similar or identical in character to the adhesive-surfaced foam tape used in the construction of the catheter's flap members, will be discussed more fully in connection with the following description of the intended procedure for favorably applying the catheter device to the penis.

By representing the intended procedure for favorably applying the catheter to the penis, FIGS. 4–8 also readily demonstrate the purpose and function of the adhesive-surfaced foamed tapes. The procedure, which may be manually performed by a clinician or by the patient himself, entails removing the cover slips 102a and 102b which reside on the adhesive surfaces 98a and 98b of the foamed tapes 96a and 96b (FIG. 4), placing the free end 122 of the penis within the catheter's mid-portion 84 near the fluid discharge opening 90, followed by moving the foamed tapes 96a and 96b upward or away from the catheter roll (FIG. 5), effecting an adhesive attachment of the foamed tapes 96a and 96b to the opposing sides of the penis 120 while the free end 122 of the penis remains satisfactorily positioned within the catheter mid-portion 84 (FIG. 6), then unrolling the catheter roll 92 in order to satisfactorily extend the catheter sleeve member 86 to cover the penis 120 and extend a substantial distance beyond the free ends 100a and 100b of the foamed tapes (FIG. 7), and completing the procedure by encircling and over lapping a closure band 110 about the sleeve member 86 and suitably above the foamed tapes 96a and 96b to sufficiently effect a liquid-tight seal between the inner surface of the sleeve member and the penis 120.

It can readily be appreciated from the foregoing that the foamed tapes, when applied to the opposing sides of the penis in the manner described, will substantially prevent the free end of the penis from being pushed away from the mid-portion of the catheter, and will substantially prevent the relatively loose penile skin from being pushed ahead of the roll when the catheter roll is unrolled over and upon the penis. It can also be readily appreciated that in a catheter requiring an encircling closure band to effect a liquid-tight seal, placing the closure band between the free ends of the foamed tapes and the free end of the sleeve member will satisfactorily prevent the leakage of urine beyond the free end of the sleeve member.

The catheter may be manually removed from the penis by first removing the closure band, by unrolling the sleeve member to a point that the sleeve member achieves its previous rolled-up state, followed by a detaching of the foamed tapes from the sides of the penis. It may not e necessary, however, in all circumstances to manually detach the adhesive tapes from the sides of the penis, as the adhesive connection therebetween may be lost over a period of time due to the action of moisture upon the adhesive interface therebetween.

In conclusion, it should be pointed out that, although the primary function of the foamed tapes is to prevent the displacement of the penis from an intended position within the catheter during the application procedure, a secondary function, being the ability of the foamed tapes to hold the penis in proper place within the catheter after the application procedure, may be realized. Also, it should be pointed out that a catheter constructed according to the present invention may utilize a continuous band of adhesive substance on the inner surface of the sleeve member for effecting a liquid-tight seal with the penis, as opposed to the arrangement whereby a closure band is utilized for the same purpose. Additionally, it should be noted that the use of two adhesive-surfaced foamed tapes according to this disclosure is by way of example only, as it would be in keeping the principles of the present invention to provide a singular foamed tape or to substitute a foamed tape for a flap member of a different type and material. Further, it should be noted that it would be in keeping with the present invention to attach the foamed tape or tapes at what would be considered the sides of the catheter roll, such tape or tapes having a general progression away from the catheter roll and parallel to the the longidudinal axis of the catheter, as opposed to what would be considered an attachment to the top of the catheter roll and a general progression perpendicular to said axis, as depicted by the figures in the drawing.

What is claimed as exclusive property or priviledge is:

1. A method of manufacturing a device for the drainage of urine from a penis, wherein said device incorporates the use of at least one unitary flap member connected thereto for assisting in a procedure for applying said device upon said penis, and wherein said device includes a stem section, a substantially conical mid-portion emerging and enlarging from said stem section, and a thin-walled sleeve member having an inner surface and dimensioned to substantially cover said penis when extended thereover from a rolled-up state, said flap member connected to said inner surface and comprising a length of flexible material having a predetermined width, providing an adhesive surface, and providing a non-adhesive surface opposing said adhesive surface, said method of manufacture including the steps of:

forming the stem section, mid-portion, and sleeve member of said device;

outwardly exposing said inner surface by rolling said sleeve member into a catheter roll which resides in the vicinity of said mid-portion;

providing a first flap member that extends rearward of said roll;

and subsequently providing a sustained connection between said first flap member and said catheter roll such that a portion of said first flap member is connected to said inner surface and is substantially longitudinally opposed by a free end of said first flap member.

2. The method of claim 1, further providing an additional flap member opposite said first flap member connected to the inner surface of said rolled catheter at said mid portion.

3. A method of applying an externally worn drainage device to a penis, wherein said device includes a rolled-up sheath member residing in the vicinity of a conical mid-portion of said drainage device, and also includes at least one unitary adhesive-surfaced flap member progressing a substantial distance away from said rolled-up sheath member whereby said flap member may adhesively engage a side of said penis, said sheath member dimensioned to substantially cover said penis when unrolled thereupon, said method including the consecutive steps of:

manually placing a free end portion of the penis within the conical mid portion of the drainage device;

extending the flap members from the rolled sheath longitudinally in a direction opposite to the free end of the penis:

placing the flap member on the penis and attaching to the penis; and unrolling the sheath member over the penis and flap member.

4. The method of claim 3, including a further step of encircling said sheath member exterior with a closure band means and placing said closure band means annularly between said flap member and a free end of said sleeve member wherein said sleeve member extends a substantial distance beyond said flap member when unrolled over said penis.

* * * * *